(12) United States Patent
Ross et al.

(10) Patent No.: US 7,896,845 B2
(45) Date of Patent: Mar. 1, 2011

(54) SURGICAL PORTAL ASSEMBLY

(75) Inventors: Adam J. Ross, Prospect, CT (US);
Michael A. Zemlok, Prospect, CT (US);
Brian Rockrohr, Waterbury, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 1 day.

(21) Appl. No.: 12/467,474

(22) Filed: May 18, 2009

(65) Prior Publication Data

US 2009/0326466 A1   Dec. 31, 2009

Related U.S. Application Data

(60) Provisional application No. 61/075,856, filed on Jun. 26, 2008.

(51) Int. Cl.
*A61M 5/178* (2006.01)
(52) U.S. Cl. .......... 604/167.01; 604/167.04; 604/167.03; 604/167.02; 604/164.01
(58) Field of Classification Search ............. 604/167.01, 604/167.03, 167.06, 164.01–167.06; 606/167
See application file for complete search history.

(56) References Cited

U.S. PATENT DOCUMENTS

| | | | |
|---|---|---|---|
| 6,033,426 A | 3/2000 | Kaji | |
| 7,347,829 B2 | 3/2008 | Mark et al. | |
| 2003/0208097 A1 | 11/2003 | Aboul-Hosn et al. | |
| 2005/0165269 A9 | 7/2005 | Aboul-Hosn et al. | |
| 2006/0217666 A1 | 9/2006 | Wenchell | |
| 2008/0051739 A1* | 2/2008 | McFarlane | 604/278 |

FOREIGN PATENT DOCUMENTS

| | | |
|---|---|---|
| EP | 1263495 | 8/2006 |
| EP | 1707133 | 10/2006 |
| WO | 0154749 | 8/2001 |
| WO | 2004032749 | 4/2004 |

OTHER PUBLICATIONS

European Search Report for corresponding EP 09251614 date of mailing is Nov. 11, 2009 (3 pages).

* cited by examiner

*Primary Examiner* — Nicholas D Lucchesi
*Assistant Examiner* — Leah Stohr

(57) ABSTRACT

A surgical portal assembly includes a portal member adapted for positioning within tissue. The portal member defines a central longitudinal axis and has a longitudinal passageway for permitting passage of a surgical object. In addition, the portal member includes a seal mount. A seal member is mounted within the seal mount of the portal member. Further, the seal member has inner surface portions defining a passage for receiving the surgical object. Aside from the seal member, the surgical portal assembly contains a plurality of seal magnets mounted to the seal member. The seal magnets are arranged with respect to the passage of the seal member whereby respective poles of the seal magnets generate an attractive force to draw the inner surface portions of the seal member about the surgical object to facilitate establishing a substantial sealing relation therewith.

16 Claims, 5 Drawing Sheets

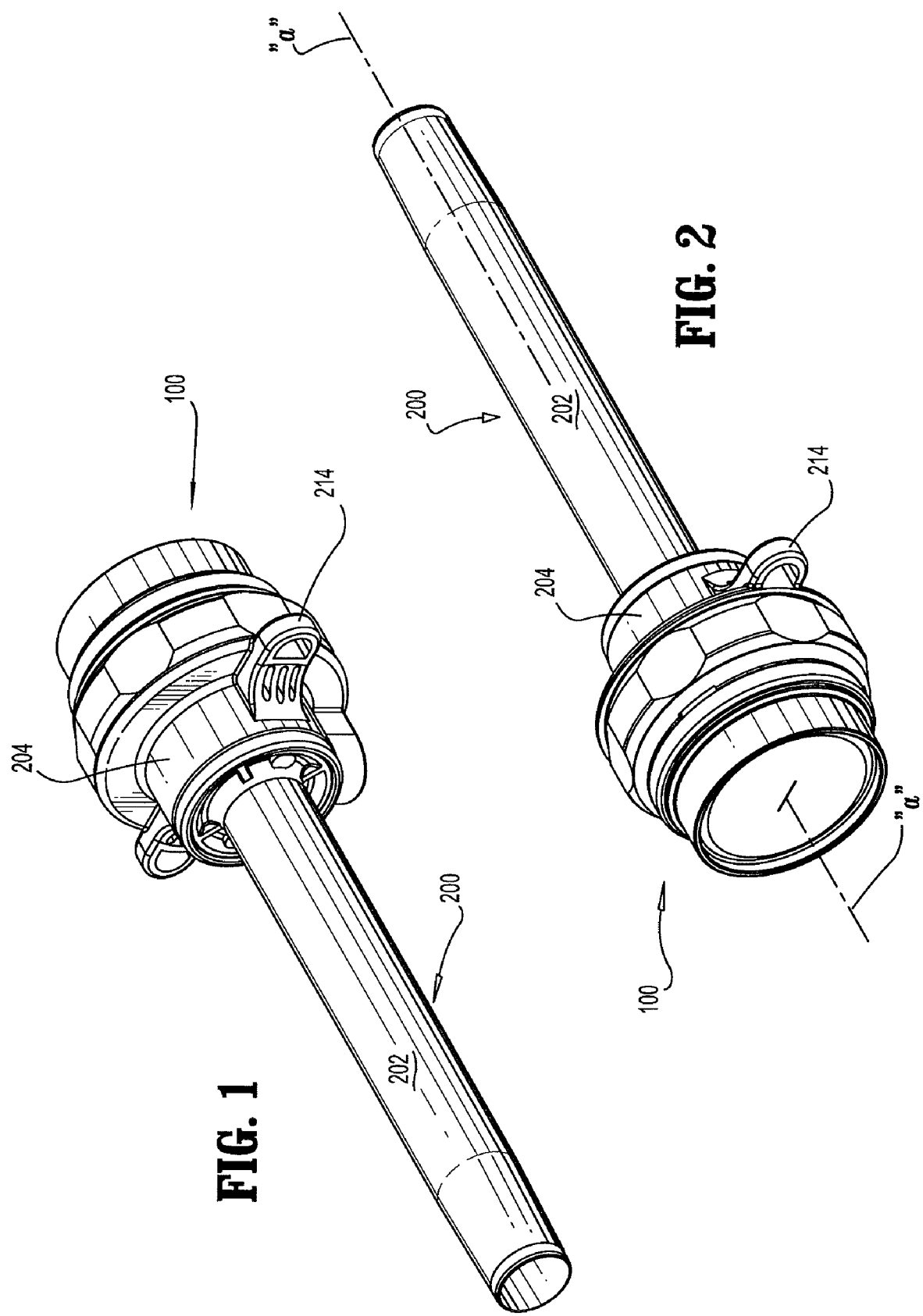

SURGICAL PORTAL ASSEMBLY

CROSS REFERENCE TO RELATED APPLICATION

The present application claims the benefit of and priority to U.S. Provisional Application Ser. No. 61/075,856, filed on Jun. 26, 2008, the entire contents of which are incorporated herein by reference.

BACKGROUND

1. Technical Field

The present disclosure relates to surgical devices and, more particularly, to surgical seal assemblies for use with a surgical access device during minimally invasive surgical procedures.

2. Description of the Related Art

Minimally invasive surgical procedures, including both endoscopic and laparoscopic procedures, permit surgery to be performed on organs, tissues and vessels far removed from an opening within the tissue. Laparoscopic and endoscopic procedures generally require that any instrumentation inserted into the body be sealed, i.e. provisions must be made to ensure that gases do not enter or exit the body through the incision as, for example, in surgical procedures in which the surgical region is insufflated. These procedures typically employ surgical instruments which are introduced into the body through a cannula. The cannula has a seal assembly associated therewith. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. However, despite its recent success and overall acceptance as a preferred surgical technique, minimally invasive surgery, such as laparoscopy, has several disadvantages. In particular, the maintenance of the seal about the surgical instrument has proved to be difficult in certain procedures, e.g., in procedures requiring extensive manipulation of the long narrow endoscopic instruments within a remote site. In addition, the force needed to insert the surgical instrument requires great effort by the user to overcome the seal's retention force.

SUMMARY

The presently disclosed surgical portal assembly includes a portal member adapted for positioning within tissue. The portal member defines a central longitudinal axis and has a longitudinal passageway for permitting passage of a surgical object. In addition, the portal member includes a seal mount. A seal member is mounted within the seal mount of the portal member. Further, the seal member has inner surface portions defining a passage for receiving the surgical object. Aside from the seal member, the surgical portal assembly contains a plurality of seal magnets mounted to the seal member. The seal magnets are arranged with respect to the passage of the seal member whereby respective poles of the seal magnets generate an attractive force to draw the inner surface portions of the seal member about the surgical object to facilitate establishing a substantial sealing relation therewith.

An embodiment of the surgical portal assembly additionally includes a plurality of mount magnets associated with the seal mount. The mount magnets are arranged to generate a repulsive force with respect to the seal magnets to repel the seal magnets thereby biasing the inner portions of the seal member toward the central longitudinal axis and about the surgical object.

A further embodiment of the surgical portal assembly incorporates first and second seal magnets mounted to the seal member. The first and second seal magnets have inner poles disposed adjacent the passage of the seal member. The inner poles of the first and second seal magnets are oppositely charged whereby attractive forces between the inner poles draw the inner surface portions of the seal member about the surgical object to facilitate establishing a substantial sealing relation therewith.

Another embodiment of the surgical portal assembly includes first and second mount magnets mounted to the seal mount and disposed radially outward relative to the central longitudinal axis. The first and second mount magnets are arranged whereby respective poles thereof are oppositely charged with respect to corresponding outer poles of the first and second seal magnets to bias the first and second seal magnets toward the central longitudinal axis.

BRIEF DESCRIPTION OF THE DRAWINGS

Embodiments of the present disclosure are described hereinbelow with reference to the drawings, wherein:

FIG. 1 is a perspective front view of a surgical portal assembly and a cannula assembly in accordance with the principles of the present disclosure;

FIG. 2 is a perspective rear view of the surgical portal assembly and a cannula assembly of FIG. 1;

DETAILED DESCRIPTION OF THE EMBODIMENTS

Figure 3:
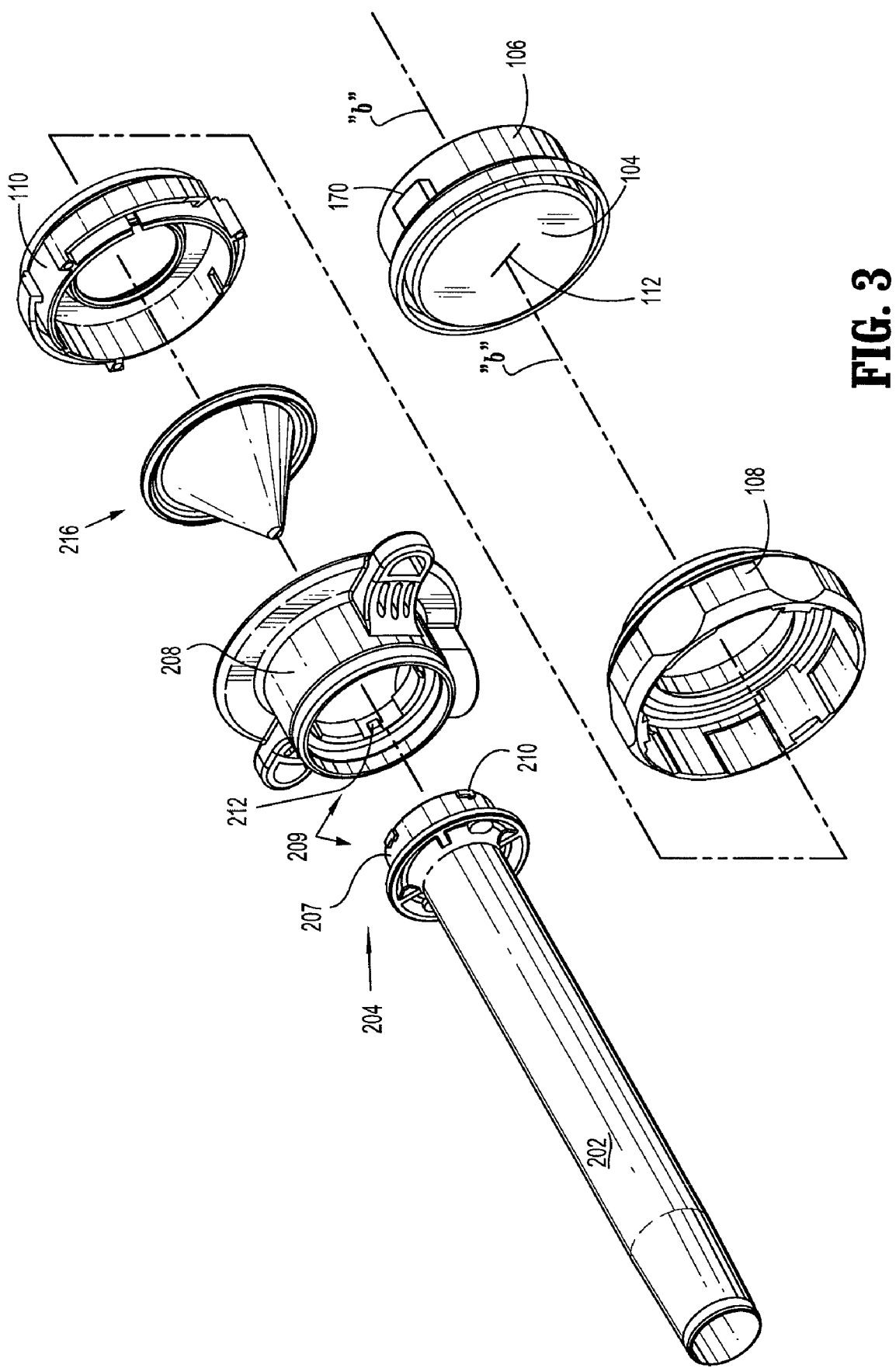
FIG. 3 is a perspective exploded view of the surgical portal assembly and the cannula assembly of FIG. 1.

The present disclosure will now describe in detail embodiments of a surgical portal assembly with reference to the drawings in which like reference numerals designate identical or substantially similar parts in each view. As used herein, "clinician" refers to a doctor, nurse or other care provider and may include support personnel. Throughout the description, the term "proximal" will refer to the portion of the assembly closest to the clinician, whereas the term "distal" will refer to the portion of the assembly farthest from the clinician.

With reference to FIGS. 1-4, a surgical portal assembly 100 is operatively attached to an access assembly 200, such as a cannula or trocar assembly. Access assembly 200 defines passageway therethrough and is particularly adapted for use in laparoscopic surgery where the peritoneal cavity is insufflated with a suitable gas, such as carbon dioxide, to separate the cavity walls from the internal organs. During a conventional laparoscope surgery, the clinician inserts an obturator assembly (not shown) through the passageway of access assembly 200. The obturator assembly may have a blunt, non-bladed, or sharp pointed distal end. Typically, the clinician uses the obturator assembly to penetrate the abdominal wall or introduce the access assembly 200 through the abdominal wall. The clinician subsequently removes the obturator from the access assembly 200 to clear passage for surgical instrumentation. The surgical instrumentation is then inserted through the access assembly 200 to conduct the appropriate surgical procedure.

Access assembly 200 includes a cannula sleeve 202 and a cannula housing 204. Cannula sleeve 202 defines a longitudinal axis "a" extending along the length of cannula sleeve 202 and contains an internal longitudinal passage 206 adapted to allow passage of surgical instrumentation. Cannula sleeve 202 may be constructed of a translucent or opaque material. Moreover, cannula sleeve 202, or any portion thereof, may be formed of stainless steel or any other suitable rigid material such as polymer or the like. The outer diameter of cannula sleeve 202 may vary to accommodate different surgical instruments. For example, the outer diameter of cannula sleeve may range from about 4.5 mm to about 15 mm. Irrespective of its size, cannula sleeve 202 is configured to be operatively coupled to surgical portal assembly 100 through cannula housing 204.

As shown in FIG. 3, cannula sleeve 202 is operatively secured to cannula housing 204 by any suitable means. In embodiment shown in FIG. 3, cannula housing 204 includes a housing flange 207 and a main housing 208. The housing flange 207 is attached to a proximal end of cannula sleeve 202. A bayonet coupling 209, or any other suitable connecting apparatus or mechanism, couples housing flange 207 to main housing 208. Specifically, bayonet coupling 209 includes radially spaced tongues 210 positioned around an external surface of housing flange 207 and corresponding recesses 212 radially spread around an internal surface of main housing 208. Tongues 210 are configured for reception within recesses 212. To attach housing flange 207 to main housing 208, a clinician has to position tongues 210 inside recesses 212 and rotate either housing flange 207 or main housing 208 to lock bayonet coupling 209.

With further reference to FIG. 3, cannula housing 204 contains a first seal member 216, such as a duckbill valve, zero closure valve, a multiple or single slit valve, a trumpet valve, a flapper valve or the like. First seal member 216 closes in the absence of a surgical instrument, in response to the pressurized environment of the insufflation gases present in the abdominal cavity, or when a combination of the mentioned conditions takes place. Conversely, when a surgical instrument is introduced through the first seal member 216, first seal member 216 expands and allows passage of the surgical instrument therethrough.

Figure 4:
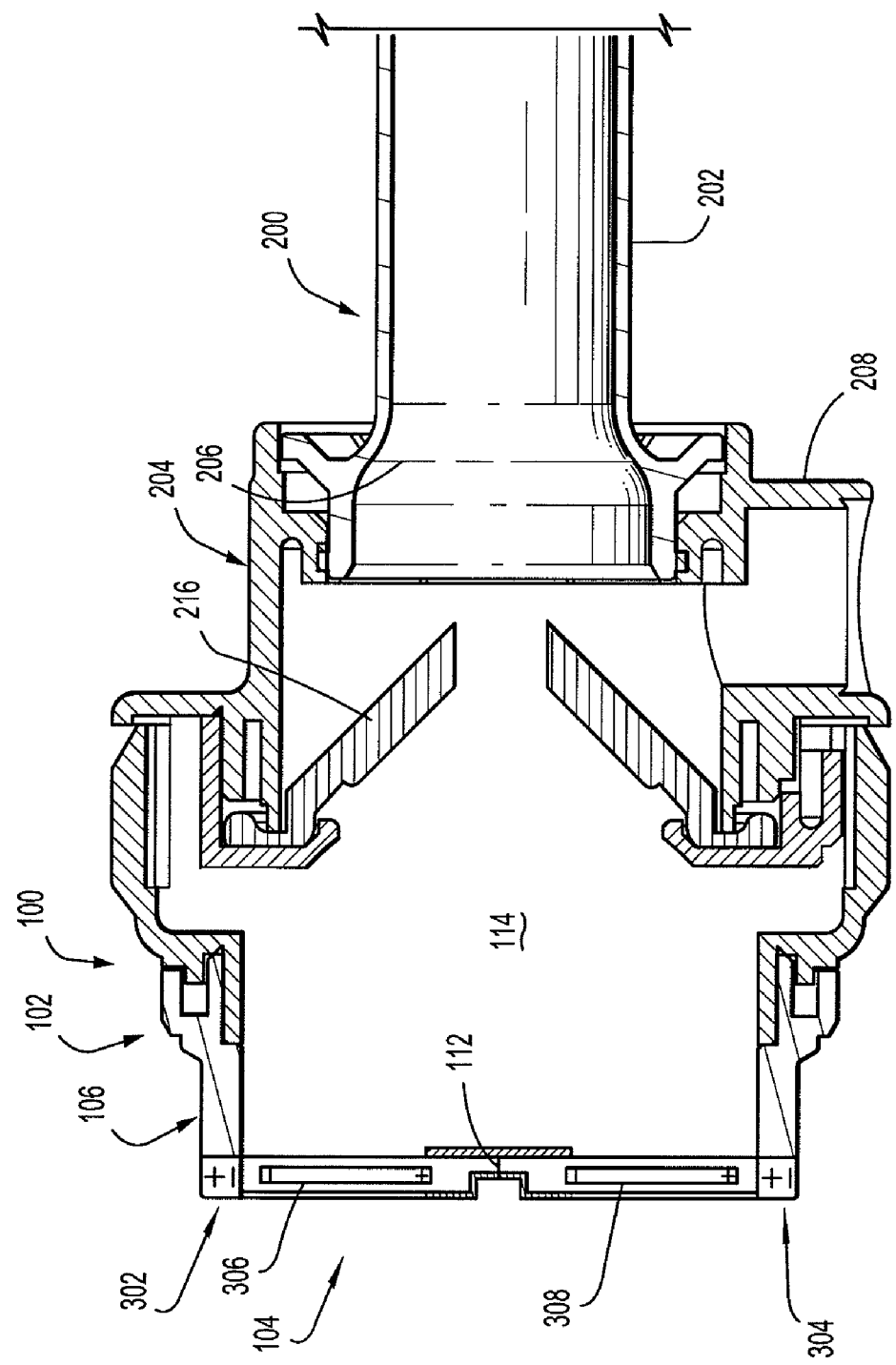
FIG. 4 is a side cross-sectional view of the surgical portal assembly of FIG. 1.

Referring to FIGS. 3 and 4, cannula housing 204 is releasably connected to a surgical port assembly 100. Surgical port assembly 100 includes a seal housing 102 defining a central seal housing axis "b" that is substantially parallel to the longitudinal axis "a" extending along the length of cannula sleeve 202. (See FIG. 2). The central housing axis "b" may even coincide with the longitudinal axis "a." Seal housing 102 further includes first, second, and third interconnected housing components 106, 108, 110. First, second, and third housing components 106, 108, 110 may be assembled together using suitable technique. Altogether, cannula housing 204 defines an internal passageway 114 to allow insertion of surgical instruments therethrough.

First housing component 106 includes a second seal member 104 mounted thereon. Second seal member 104 is made of a pliable material, such as polyisoprene, natural rubber, soft urethane, silicone, or the like. In addition, seal member 146 defines a slit or aperture 112 positioned in an inner portion thereof for permitting passage of a surgical instrument therethrough. During use, second seal member 104 forms a seal about a surgical instrument inserted through the slit 112. When a surgical instrument is inserted through slit 112, second seal member 104 conforms to the shape of the inserted surgical instrument and forms a seal about the surgical instrument. Upon removal of the surgical instrument, slit 112 returns to its closed position and inhibits fluid transfer between internal passageway 114 and the exterior of cannula housing 204.

With further reference to FIG. 4, cannula housing 204 further includes first and second magnets 302, 304 mounted on the first housing component 106 in a diametrical opposed relation. Each of first and second magnets 302, 304 is arranged so that an inner pole is positioned closer to slit 112 and an outer pole is positioned farther from slit 112. The inner poles of first and second magnets 302, 304 have opposite charges and are configured to interact electromagnetically with the outer poles of third and fourth magnets 306, 308.

Second seal member 104 has third and fourth magnets 306, 308 imbedded therein. Each of third and fourth magnets 304, 308 is arranged such an inner pole is closer to the slit 112 and an outer pole is farther from the slit 112. The outer poles of third and fourth magnets 306, 308 have opposite charges. Furthermore, the inner pole of first magnet 302 and the outer pole of third magnet 306 have like charges, as seen in FIG. 4. Consequently, the electromagnetic field induced by first and third magnets 302, 306 causes a repulsion force between the inner pole of first magnet 302 and the outer pole of third magnet 306. Since first magnet 302 is fixed to first housing component 106 and third magnet 306 is imbedded to pliable second seal member 104, the repulsion force caused by the electromagnetic field causes third magnet 306 to move toward slit 112. Given that third magnet 306 is embedded in second seal member 104, the portion of second seal member 104 surrounding third magnet 306 moves toward slit 112 and aids in the formation of a seal. Similarly, the inner pole of second magnet 304 and the outer pole of fourth magnet 308 have like charges. Thus, the electromagnetic filed induced by second and fourth magnets 304, 308 causes a repulsion force between the inner pole of second magnet 304 and the outer pole of fourth magnet 308. Because second magnet 304 is fixed to first housing component 106 and fourth magnet 308 is imbedded to pliable second seal member 104, the repulsion forced caused by the electromagnetic filed causes fourth magnet 308 to move toward slit 112. Since fourth magnet 308 is imbedded in second seal member 104, the portion of second seal member 104 surrounding fourth magnet 308 moves toward slit 112 and aids in the formation of a seal.

Moreover, the inner poles of third and fourth magnets 306, 308 have opposite charges and thus attract each other. The attraction force between the inner poles of third and fourth magnets 306, 308 causes the portions of second seal member 104 surrounding third and fourth magnets 306, 308 to move toward slit 112, thereby aiding the formation of a seal.

Figure 5:
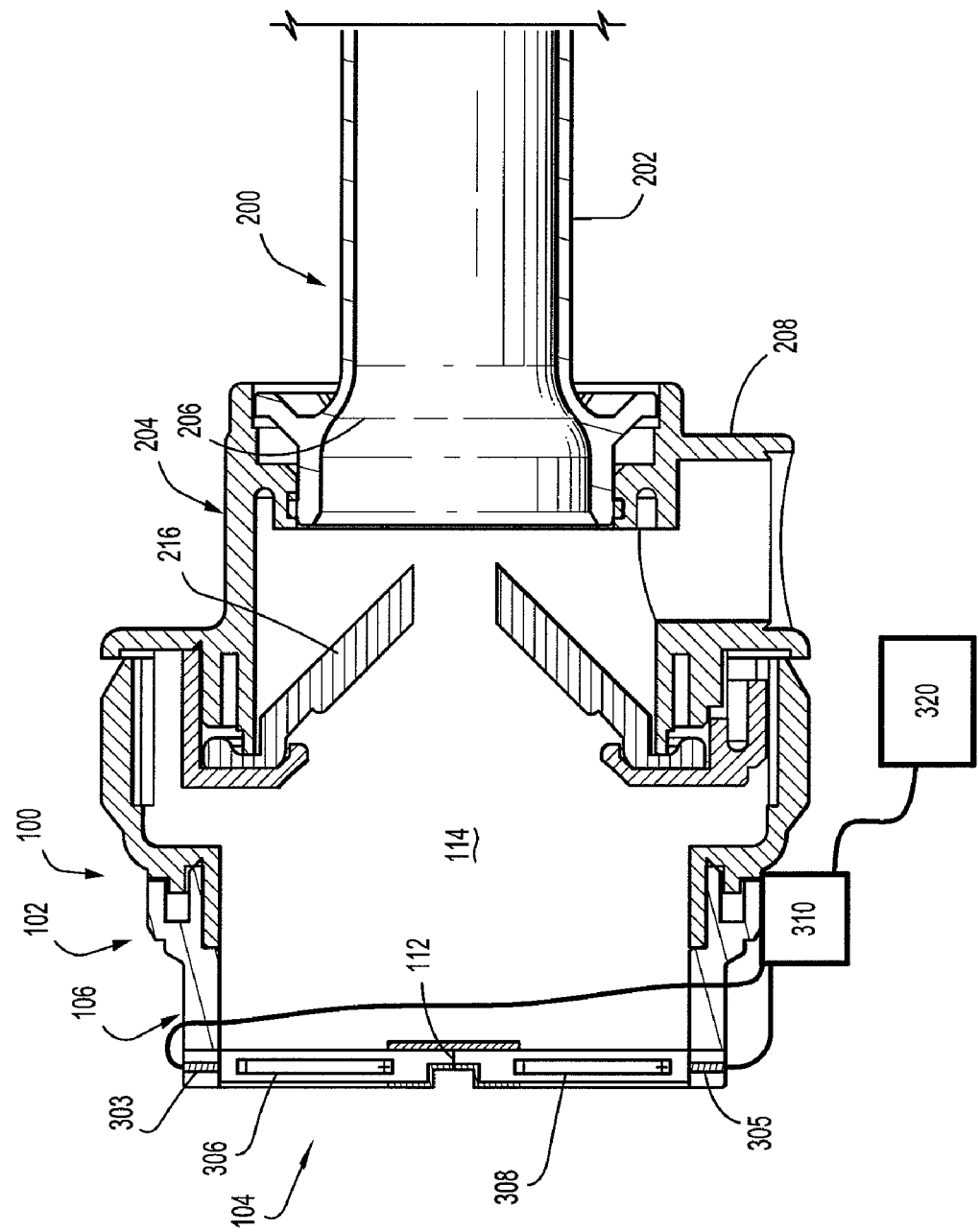
FIG. 5 is a side cross-sectional view of the surgical portal assembly of FIG. 1 with electromagnets.

As shown in FIG. 5, cannula housing 204 may include first and second electromagnets 303, 305 instead of first and second magnets 302, 304. Like first and second magnets 302, 304, first and second electromagnets 303, 305 are secured to first housing component 106 and are arranged so that their electromagnetic fields induce repulsive forces that repel or move third and fourth magnets 306, 308 toward slit 112, thus assist the formation of a seal around slit 112. The repulsive force of first and second electromagnetic 303, 305, however, may be controlled by electronic circuitry 310. Hence, first and second electromagnets, which may be formed by one or more coils, are disposed in electrical connection with electronic circuitry 310. Electronic circuitry 310 is operatively connected to a power source 320 and is adapted to control the repulsive force produce by first and second electromagnets 303, 305. Power source 320 supplies electronic circuitry 310 and first and second electromagnets 303, 305 the power necessary to function properly.

Figure 6:
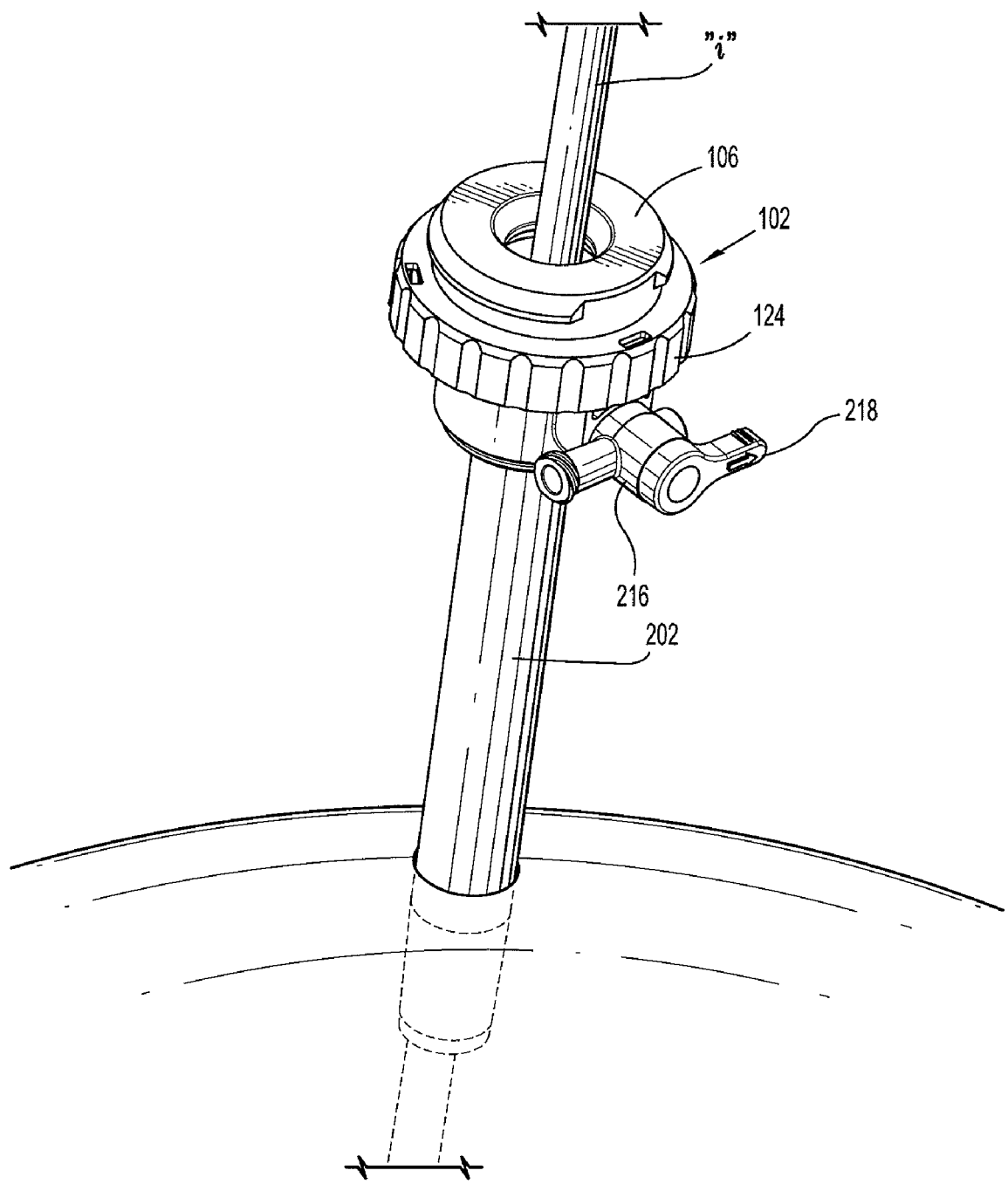
FIG. 6 is perspective view illustrating the surgical portal assembly and a cannula assembly of FIG. 1 accessing an internal cavity with a surgical instrument inserted therethrough.

During operation, the clinician initially introduces access assembly 200 into an insufflated abdominal cavity, as shown in FIG. 6. Then, the clinician inserts a surgical instrument "i" into surgical port assembly 100 and advances surgical instrument "i" through passage 114 of seal housing 102. As surgical instrument "i" passes through slit 112, the attractive and repulsive forces generated by first, second, third, and fourth magnets 302, 304, 306, 308 draw portions of second seal member 104 toward slit 112 and surgical instrument "i" and consequently facilitate the formation of a seal between surgical instrument "i" and second seal member 104. As a result, second seal member 104 engages surgical instrument "i" in a substantial sealing relation. The clinician thereafter further advances surgical instrument "i" toward the body cavity through cannula sleeve 202. Once the surgical instrument reaches the desired surgical site, the clinician may commence the appropriate surgical procedure.

In the case of the embodiment shown in FIG. 5, the clinician may control the repulsive forces of the first and second electromagnets 303, 305 with electronic circuitry 310 before, during, or after inserting surgical instrument "i" through slit 112. To regulate these repulsive forces, the clinician controls the power output by power source 320. An increase in the power supplied to the electronic circuitry 310 increases the repulsive forces generated by first and second electromagnets 303, 305, causing portions of second seal member 104 to move further toward slit 112. Conversely, a decrease in the power supplied to electronic circuitry 310 decreases the repulsive forces generated by first and second electromagnets 303, 305, thereby diminishing the advancement of portions of second seal member 104 toward slit 112.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What it claimed is:

1. A surgical portal assembly, which comprises:
    a portal member adapted for positioning at least partially within tissue, the portal member defining a central longitudinal axis and having a longitudinal passageway for permitting passage of a surgical object, the portal member including a seal mount;
    a seal member mounted within the seal mount of the portal member, the seal member comprising a pliable material and having inner surface portions defining a passage for receiving the surgical object; and
    a plurality of seal magnets at least partially embedded within the pliable material of the seal member, the seal magnets arranged in general diametrical opposed relation on opposed sides of the passage of the seal member whereby respective poles of the seal magnets generate an attractive force to draw the inner surface portions defining the passage about the surgical object to facilitate establishing a substantial sealing relation therewith.

2. A surgical portal assembly which comprises:
    a portal member adapted for positioning at least partially within tissue, the portal member defining a central longitudinal axis and having a longitudinal passageway for permitting passage of a surgical object, the portal member including a seal mount;
    a seal member mounted within the seal mount of the portal member, the seal member having inner surface portions defining a passage for receiving the surgical object;
    a plurality of seal magnets mounted to the seal member, the seal magnets arranged with respect to the passage of the seal member whereby respective poles of the seal magnets generate an attractive force to draw the inner surface portions of the seal member about the surgical object to facilitate establishing a substantial sealing relation therewith; and
    a plurality of mount magnets associated with the seal mount, the mount magnets arranged to generate a repulsive force with respect to the seal magnets to repel the seal magnets thereby biasing the inner portions of the seal member toward the central longitudinal axis and about the surgical object.

3. The surgical portal assembly according to claim 2 including first and second seal magnets mounted to the seal member, the first and second seal magnets having inner poles disposed adjacent the passage of the seal member, the inner poles of the first and second seal magnets being oppositely charged whereby attractive forces between the inner poles draw the inner surface portions of the seal member about the surgical object to facilitate establishing a substantial sealing relation therewith.

4. The surgical portal assembly according to claim 3 including first and second mount magnets mounted to the seal mount and disposed radially outward relative to the central longitudinal axis, the first and second mount magnets arranged whereby respective poles thereof are oppositely charged with respect to corresponding outer poles of the first and second seal magnets to bias the first and second seal magnets toward the central longitudinal axis.

5. The surgical portal assembly according to claim 1 wherein the seal magnets are fully embedded within the pliable material of the seal member.

6. The surgical portal assembly according to claim 1 wherein the pliable material comprises an elastomeric material.

7. The surgical portal assembly according to claim 1 wherein the seal magnets are dimensioned and adapted to cooperate with the seal member such that the passage of the seal member is substantially closed in the absence of the surgical object.

8. A surgical portal assembly, which comprises:
    a portal member adapted for positioning at least partially within tissue, the portal member defining a central longitudinal axis and having a longitudinal passageway for permitting passage of a surgical object;
    a seal member mounted to the portal member and intersecting the longitudinal passageway, the seal member comprising a pliable material having inner surface portions defining a passage for receiving the surgical object; and
    first and second seal magnets mounted to the inner surface portions of the seal member, the first and second seal magnets having inner poles disposed on each side of the passage, the inner poles of the first and second seal magnets being oppositely charged whereby attractive forces between the inner poles draw the inner surface portions of the seal member about the surgical object to facilitate establishing a substantial sealing relation therewith.

9. The surgical portal assembly according to claim 8 wherein the inner poles of the first and second seal magnets are dimensioned and adapted to cooperate with the inner surface portions of the seal member such that the passage is substantially closed in the absence of the surgical object.

10. The surgical portal assembly according to claim 8 wherein the first and second seal magnets are at least partially embedded within the inner surface portions of the seal member.

11. The surgical portal assembly according to claim 10 wherein the seal magnets are fully embedded within the inner surface portions of the seal member.

12. The surgical portal assembly according to claim 8 wherein the passage of the seal member is in general longitudinal alignment with the central longitudinal axis of the portal member.

13. The surgical portal assembly according to claim 12 wherein the inner poles of the first and second seal magnets are arranged in diametrical opposed relation relative to the inner passage and along a line of intersection with the central longitudinal axis.

14. The surgical portal assembly according to claim 8 wherein the inner poles of the first and second seal magnets are dimensioned and adapted to cooperate with the inner surface portions of the seal member such that the passage is substantially open in the absence of the surgical object.

15. The surgical portal assembly according to claim 8 including a zero closure valve mounted to the portal member, the zero closure valve dimensioned and adapted to substantially close in the absence of the surgical object.

16. The surgical portal assembly according to claim 8 including first and second portal magnets mounted relative to the portal member and disposed radially outward relative to the central longitudinal axis, the first and second portal magnets arranged whereby respective poles thereof are oppositely charged with respect to corresponding outer poles of the first and second seal magnets to bias the first and second seal magnets toward the central longitudinal axis.

\* \* \* \* \*